(12) United States Patent
Basom et al.

(10) Patent No.: US 6,688,161 B1
(45) Date of Patent: Feb. 10, 2004

(54) PERCHLORATE ANALYSIS DEVICE AND METHOD

(75) Inventors: Kenneth E. Basom, Waldorf, MD (US); Laura A. Tinsley, Port Tobacco, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/113,638

(22) Filed: Mar. 29, 2002

(51) Int. Cl.[7] .................. G01N 30/00; G01N 30/48; G01N 30/96
(52) U.S. Cl. .............. 73/61.52; 73/61.53; 422/70; 436/161; 210/656
(58) Field of Search ............... 73/23.35, 23.39, 73/61.52, 61.53, 61.55; 422/70; 436/161; 210/656

(56) References Cited

U.S. PATENT DOCUMENTS

| | | | | |
|---|---|---|---|---|
| 3,926,559 A | * | 12/1975 | Stevens | 436/161 |
| 4,265,634 A | * | 5/1981 | Pohl | 436/161 |
| 4,272,246 A | * | 6/1981 | Fritz et al. | 436/161 |
| 5,597,481 A | * | 1/1997 | Stillian et al. | 210/198.2 |
| 5,618,502 A | * | 4/1997 | Byers et al. | 423/70 |
| 6,444,475 B1 | * | 9/2002 | Anderson, Jr. et al. | 436/161 |
| 2001/0019031 A1 | * | 9/2001 | Anderson, Jr. et al. | 210/656 |
| 2003/0075508 A1 | * | 4/2003 | Woodruff et al. | 210/683 |

* cited by examiner

*Primary Examiner*—Daniel S. Larkin
(74) *Attorney, Agent, or Firm*—Mark Homer

(57) ABSTRACT

The present invention comprises a device and method of analyzing trace amounts of perchlorate in liquid samples comprising a concentrator column used in an ion chromatographic system that comprises an anionic capacity ranging from about 0.030 microequivalents per column to about 0.060 microequivalents per column and capable of removing substantially all perchlorate from the sample and using a multi-directional flow through said concentrator column in order to enhance perchlorate detection. The invention also comprises a packing material comprising from about 25 percent to about 80 percent of a low anionic capacity material comprising an anionic capacity of less than about 0.03 milliequivalents per milliliter mixed with from about 25 percent to about 80 percent of a high anionic capacity material comprising a anionic capacity of more than about 0.07 milliequivalents per milliliter. The device and method of the present invention reduces interference from other ions within a sample allowing the perchlorate analysis to be 100 to 1000 times more sensitive than current analysis methods.

15 Claims, 2 Drawing Sheets

PERCHLORATE ANALYSIS DEVICE AND METHOD

STATEMENT OF GOVERNMENT INTEREST

The invention described herein may be manufactured and used by or for the Government of the United States of America for governmental purposes without payment of any royalties thereon or therefor.

BACKGROUND OF THE INVENTION

1. Field of the Invention

This invention relates to a device and method for use in an ion chromatographic system for the analysis of trace levels of perchlorate. More particularly, the device and method concentrates perchlorate and reduces the level of interference from other matrix bound components in a test specimen, thereby enhancing the detection of the perchlorate within the test specimen.

2. Description of the Related Art

Perchlorate is a chemical that exists in the environment as a part of other compounds, such as ammonium, potassium, or sodium perchlorate. Ammonium perchlorate, which comprises the bulk of manufactured perchlorate, is used as an oxygen-adding component in solid fuel propellant for rockets, missiles, and fireworks. Because of its limited shelf-life, inventories of ammonium perchlorate must be periodically replaced. Thus, large volumes of the compound have been disposed of since the 1950's.

Until recently, perchlorate containing compounds were not suspected as being detrimental to health. In fact, potassium perchlorate was used therapeutically to treat hyperthyroidism. However, recent studies have shown that perchlorate can affect the thyroid gland, and, therefore, affect metabolism, growth, and development. Due to these studies, the federal Environmental Protection Agency (EPA) has put perchlorate on its Contaminant Candidate List for further study and potential regulatory action. Both California and Nevada have set action levels of eighteen parts per billion for perchlorate under their drinking water regulations. In a report published in January of 2002, the EPA have set a proposed action limit for perchlorate at 1.5 parts per billion. Because current regulatory actions regarding perchlorate have begun and future regulatory actions regarding perchlorate appear certain, regulatory agencies have focused upon testing methods for perchlorate.

The only current method of detecting perchlorate in samples found by the regulatory agencies is using ion chromatography. This method of detection applies two basic components: (1) separation of perchlorate from all other species in a sample, and (2) measurement of the separated perchlorate against suitable standards. Separation of perchlorate in a sample is based upon the attraction of perchlorate for a special organic exchanger packed into a column. The anionics are carried through the column by a flow of solution. As the anionics move through the column, they separate into thin bands. Because the relative strength of the attraction of the different anionics to the ion exchanger is different for each of the species dissolved in the sample, they separate and elute from the ion exchange column at different times. As the anionics pass through the detector, the detector response is registered as peaks with a peak amplitude proportional to concentration and at a retention time characteristic of the anionic. This is accomplished through a specific conductance detector that measures the conductance relative to the background which is generated by the mobile phase carrying the analyte through the system.

The hardware used for this type of analysis is standard equipment used in ion chromatographic systems. The current federal EPA published method for detecting perchlorate calls for an ion chromatographic system comprised of an ion chromatographic pump, sample injection valve, guard column, analytical column, suppressor device, and conductivity detector. However, there are problems associated with obtaining low levels of perchlorate in certain types of samples using this standard ion chromatography configuration. Interferences caused by a large amount of anionics other than perchlorate within a sample can lead to false positives and/or reduced detection limits. The federal EPA method suggests that pretreating the sample through dilution can potentially assist with these problems, but the dilution may cause a reduction of the concentration of the target analyte to the point where it becomes undetectable. These problems are especially problematic in samples obtained from sources that contain extremely complex matrices of components, such as seawater. In practice, this current detection method is capable of relatively low detection levels of perchlorate in samples with low levels of ionic interferences. However, prior to the present invention, no known analysis method or device can meet the proposed action limit being considered by the EPA mentioned above.

SUMMARY OF THE INVENTION

The present invention solves the problems noted above related to the standard ion chromatographic method of perchlorate detection. The present invention comprises using a concentrator column, optimized to remove all of the perchlorate within a sample, in order to dramatically increase the overall effectiveness of detection of perchlorate within an ion chromatograph system, while reducing the waste produced by the system, and providing significantly shorter analysis times. By using the present invention, the sensitivity of perchlorate detection is increased by one hundred to one thousand times that of the current detection method described above.

Accordingly, an object of this invention is to increase the sensitivity of perchlorate detection in liquid samples.

A further object of the invention is to allow detection of low amounts of perchlorate in samples with complex matrices of ions.

This invention accomplishes these objectives and other needs related to perchlorate detection in environmental matrices by providing a device used within an ion chromatograph system to analyze the content of perchlorate within a sample. The device consists of a concentrator column that is optimized to remove all of the perchlorate within a sample while providing for minimum waste produced by the system. This is due to using a packing material within the concentrator column that has a high affinity for perchlorate ions, but a lower affinity for other high ionic organic or inorganic interferants. The concentrator column accomplishes these tasks by using a packing material comprising an anionic capacity of from about 0.030 to about 0.060 microequivalents per column, with a preferred anionic capacity of from about 0.035 to about 0.040 microequivalents per column, and a most preferred anionic capacity of about 0.036 microequivalents per column. Although applicant is unaware of any commercial packing material having such a capacity, this invention also includes such a packing material produced by blending currently available packing materials, having anionic capacities that are higher and lower than these capacities. The improved packing material is made from blending a material comprising from about twenty-five percent to about eighty percent of a low anionic capacity material comprising an anionic capacity of less than about 0.03 milliequivalents per milliliter mixed with another material comprising from about twenty-five percent to about eighty percent of a high anionic capacity material comprising an anionic capacity of more than about 0.07 milliequivalents per milliliter. The invention also includes using the concentrator column device described above within an ion chromatographic system in order to detect trace levels of perchlorate in water samples.

BRIEF DESCRIPTION OF THE DRAWINGS

The accompanying drawings, which are incorporated in and constitute a part of the specification, illustrate embodiments of the invention, and, together with the description, serve to explain the principles of the invention.

DESCRIPTION OF THE PREFERRED EMBODIMENT

The invention, as embodied herein, comprises a device used within an ion chromatograph system to analyze the content of perchlorate within a sample. The standard injection loop is replaced with a concentrator column. The concentrator column is packed with a material comprising an anionic capacity of from about 0.030 to about 0.060 microequivalents per column, with a preferred anionic capacity of from about 0.035 to about 0.040 microequivalents per column, and a most preferred anionic capacity of about 0.036 microequivalents per column. This range of anionic capacity allows for removal of substantially all perchlorate from a sample while minimizing the waste produced during the removal process. This capacity will also optimally decrease the analysis time per sample. Depending upon the size of the concentrator column used, such a packing material may made from blending from about twenty-five percent to about eighty percent of a low anionic capacity material comprising an anionic capacity of less than about 0.03 milliequivalents per milliliter mixed with from about twenty-five percent to about eighty percent of a high anionic capacity material comprising an anionic capacity of more than about 0.07 milliequivalents per milliliter. The use of the concentrator column packed with the above material greatly increases the effective capacity of the system and allows an analysis level from one hundred to one thousand times more effectively sensitive than the current prior art method.

Figure 1:
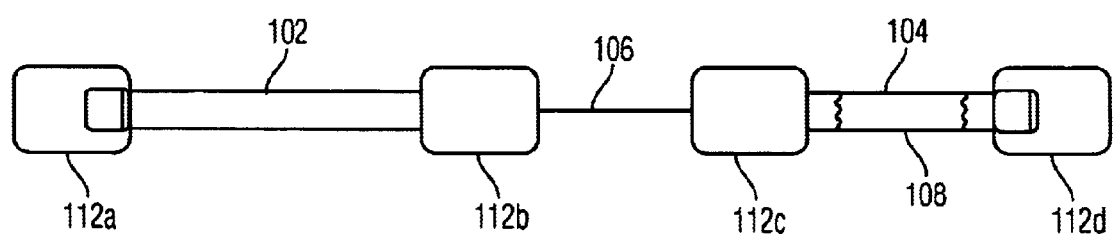
FIG. 1 shows an embodiment of the concentrator column of the present invention along with a packing column.

Referring to FIG. 1, the device consists of a concentrator column 104 that is positioned as part of a standard ion chromatographic system. In its preferred embodiment, the concentrator column 104 is loaded with packing material 108 by using a loading column 102 connected to the concentrator column 104 through tubing 106. The concentrator column 104 may comprise a fluoropolymer column body having an internal diameter of from about 4.6 millimeters to about 7.5 millimeters and a length of from about 30 millimeters to about 50 millimeters. This internal diameter may be approximately twenty percent larger than an internal diameter of commonly used concentrators and allows for a larger volume of material to be packed within the concentrator 104. The selected size of the concentrator column 104 will depend upon the anionic capacity of the packing material 108 selected for use in the column 104. The loading column 102 and concentrator column 104 may also have end assemblies 112a, 112b, 112c, and 112d. In a preferred embodiment for loading the concentrator column 104, two of the end assemblies 112a and 112d contain frits. Preferably, the loading column 102 has a length of about twice that of the concentrator column 104 and the tubing 106 is standard chromatographic tubing of approximately one to two inches in length.

The packing material 108, normally in the form of a slurry, is loaded into the loading column 102. The packing material 108 comprises an anionic capacity of from about 0.030 to about 0.060 microequivalents per column, with a preferred anionic capacity of from about 0.035 to about 0.040 microequivalents per column, and a most preferred anionic capacity of about 0.036 microequivalents per column. Currently, applicant is unaware of any known commercial packing materials having such an anionic capacity. The anionic capacity of a packing material 108 is dependent upon the shape of the particles within the material along with the coating used on said particles. These two physical characteristics may be adjusted to adjust the overall anionic capacity of the material. Rather than attempt such a complex endeavor, an alternate method of obtaining a packing material 108 having the anionic capacity discussed above is by blending two commercially available packing materials. Such a packing material 108 comprises from about twenty-five percent to about eighty percent of a low anionic capacity material comprising an anionic capacity of less than about 0.03 milliequivalents per milliliter blended with from about twenty-five percent to about eighty percent of a high anionic capacity material comprising an anionic capacity of more than about 0.07 milliequivalents per milliliter. In one embodiment of the invention, these materials are blended using an organic solvent. Preferred packing materials 108 will comprises a methacrylate base and an alkanol-quaternary amidic functional group. In a preferred embodiment of the invention approximately seventy percent of the high anionic capacity material is blended with approximately thirty percent of the low anionic capacity material to form the packing material 108. The high anionic capacity material and low anionic capacity material are normally blended into a slurry using an organic solvent such as methanol or acetonitrile. The high anionic capacity material preferably comprises an anionic capacity of from about 0.090 milliequivalents per milliliter to about 0.10 milliequivalents per milliliter, and more preferably approximately 0.095 milliequivalents per milliliter. A preferred high anionic capacity material is Allsep A-2 Anion manufactured by Alltech. The low anionic capacity material preferably comprises an anionic capacity of from about 0.015 milliequivalents per milliliter to about 0.025 milliequivalents per milliliter and more preferably comprises an anionic capacity of approximately 0.02 milliequivalents per milliliter. A preferred low anionic capacity material is Allsep Anion manufactured by Alltech. The above ratios of materials that can be blended to optimize the packing material to provide the appropriate overall column 104 capacity may differ slightly depending upon the size concentrator column 104 selected.

Figure 2:
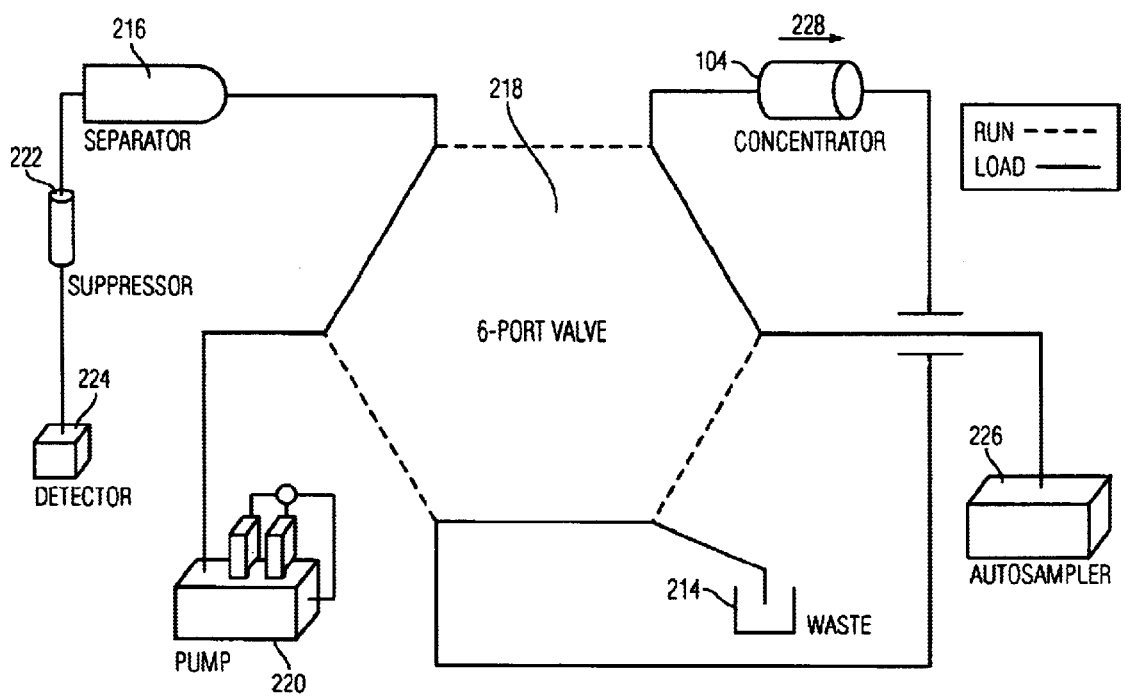
FIG. 2 shows a preferred ion chromatographic system with the concentrator column of the present invention replacing the standard injection loop.

The present invention also comprises a method of detecting trace amounts of perchlorate by using the device described above within an ion chromatographic system. Referring to FIGS. 1 and 2, the concentrator column 104 is connected to an ion chromatographic system in place of a standard ion injection loop. In operation, the concentrator column 104 is flushed with an eluent to remove the mobile phase within the column 104 from any previous runs. A six-port valve 218 is initially set so an autosampler 226 moves several milliliters of a sample to the concentrator column 104 in a first direction 228. Due to the concentrator column's 104 strong affinity for perchlorate, as described above, the perchlorate within the sample adheres to the head of the concentrator column 104 through ion exchange of the ion sites available on the packing within the column 104. Although some of the other interfering ions present in the sample adhere further down the concentrator column 104, the majority of interfering ions pass through the column as waste. The concentrator column 104 is flushed in the first direction 228 with an eluent that will drive ions other than perchlorate off the column 104. This eluent normally will not have an affinity for perchlorate to ensure that the perchlorate remains within the column 104. A preferred eluent is water. The waste is directed into a waste container 214. The 6-port valve 218 is then switched so the pump 220 sends a reagent eluent in a direction opposite to the first direction 228 through the concentrator column 104 to remove the perchlorate from the column 104. The reagent eluent is selected to have a high affinity for perchlorate to ensure removal of all of the perchlorate from the column 104. A preferred reagent eluent comprises a mixture of tetrabutylammonium hydroxide, sodium carbonate, acetonitrile, and boric acid. Preferred ratios of these constituents comprise about 6 millimolar of tetrabutylammonium hydroxide, in a solution of 15% acetonitrile and 85% water with 13 grams of boric acid per liter of water and 0.20 to 0.25 grams of sodium carbonate per liter of water. The flow containing the perchlorate is then directed to a separator 216 which provides separation through ion interactive chromatography (IIC). The separator 216 operates by the mobile phase (eluent with perchlorate) being on one side of a membrane with a substance on the other side of the membrane that provides protons through the membrane to the mobile phase. A preferred proton providing substance is a dilute sulfuric acid, most preferred is about a 9 millimolar sulfuric acid solution. The separator 216 will preferably comprise a smaller than normal diameter of approximately 2.1 mm, which is known as a pencil column in the art. The flow then leaves the separator 216 and is sent to a suppressor 222 in order to lower background conductance. Due to the lower conductance of the eluent, the suppressor 222 provides better reduction in background conductance than occurs in prior art ion chromatograph systems. Finally, the analyte is sent to a detector 224 to provide the final analysis of the sample.

The enrichment of the target analyte and removal of interference by using the above method allows detection of perchlorate ranging from one hundred to one thousand times more sensitive than when using current prior art methods.

Finally, the present invention also comprises a packing material, as described above, for a concentrator column in an ion chromatography system that is produced by the process described above. The packing material may be blended using different ratios than specifically set forth above to provide the overall capacity desired within a concentrator column depending upon the size of the column as also discussed above.

What is described are specific examples of many possible variations of the same invention and are not intended in a limiting sense. The claimed invention can be practiced using other variations not specifically described above.

What is claimed is:

1. A device used within an ion chromatograph system to analyze the content of perchlorate within a sample, comprising:
   a concentrator column; and
   a packing material packed within the concentrator column comprising an anionic capacity ranging from about 0.030 microequivalents per column to about 0.060 microequivalents per column and capable of removing substantially all perchlorate from the sample.

2. The device of claim 1, wherein the packing material comprises an anionic capacity ranging from about 0.035 microequivalents per column to about 0.040 microequivalents per column.

3. The device of claim 2, wherein the packing material comprises an anionic capacity of about 0.036 microequivalents per column.

4. The device of claim 1, wherein the packing material comprises from about twenty-five percent to about eighty percent of a low anionic capacity material comprising an anionic capacity of less than about 0.03 milliequivalents per milliliter blended with from about twenty-five percent to about eighty percent of a high anionic capacity material comprising an anionic capacity of more than about 0.07 milliequivalents per milliliter.

5. The device of claim 4, wherein the material comprises about seventy percent of the high capacity packing material blended with about thirty percent of the low capacity material.

6. The device of claim 5, wherein the concentrator comprises an internal diameter of from about 4.6 millimeters to about 7.5 millimeters and comprises a length of from about 30 millimeters to about 50 millimeters.

7. The device of claim 6, wherein the high capacity material comprises an anionic capacity of from about 0.090 milliequivalents per milliliter to about 0.10 milliequivalents per milliliter.

8. The device of claim 7, wherein the low anionic capacity material comprises an anionic capacity of from about 0.015 milliequivalents per milliliter to about 0.025 milliequivalents per milliliter.

9. The device of claim 8, wherein the high anionic capacity material comprises an anionic capacity of approximately 0.095 milliequivalents per milliliter.

10. The device of claim 9, wherein the low anionic capacity material comprises an anionic capacity of approximately 0.02 milliequivalents per milliliter.

11. The device of claim 10, wherein the packing material comprises a methacrylate base.

12. The device of claim 11, wherein the packing material comprises an alkanol-quaternary amidic functional group.

13. The device of claim 12, further comprising an organic solvent used to blend the high anionic capacity material with the low anionic capacity material.

14. The device of claim 13, wherein the high capacity material comprises Allsep A-2 Anion.

15. The device of claim 14, wherein the low capacity material comprises Allsep Anion.

\* \* \* \* \*